(12) United States Patent
Fujimoto (10) Patent No.: US 7,824,916 B2
(45) Date of Patent: Nov. 2, 2010

(54) SHEATH LIQUID FOR PARTICLE ANALYZER

(75) Inventor: Yukie Fujimoto, Kobe (JP)

(73) Assignee: Sysmex Corporation, Hyogo (JP)

( * ) Notice: Subject to any disclaimer, the term of this patent is extended or adjusted under 35 U.S.C. 154(b) by 177 days.

(21) Appl. No.: 11/699,551

(22) Filed: Jan. 30, 2007

(65) Prior Publication Data

US 2007/0177146 A1 Aug. 2, 2007

(30) Foreign Application Priority Data

Jan. 31, 2006 (JP) ............................. 2006-021672

(51) Int. Cl.
*G01N 33/48* (2006.01)
*G01N 21/00* (2006.01)

(52) U.S. Cl. ................ 436/63; 436/8; 436/10; 436/18; 436/164; 436/166; 436/172; 436/174; 252/408.1; 356/338

(58) Field of Classification Search .................. 436/8, 436/10, 17, 18, 63, 164, 166, 172, 174; 252/408.1; 422/82.05, 82.08, 82.09; 356/338, 73
See application file for complete search history.

(56) References Cited

U.S. PATENT DOCUMENTS

| 5,259,368 | A | * | 11/1993 | Wiksell ........................ 601/4 |
| 5,290,555 | A | * | 3/1994 | Guthauser et al. ........... 424/401 |
| 5,790,727 | A | * | 8/1998 | Dhadwal et al. ............... 385/38 |
| 5,935,857 | A | * | 8/1999 | Riesgo et al. ................. 436/18 |
| 6,750,060 | B2 | | 6/2004 | Ozasa et al. |
| 6,872,695 | B1 | * | 3/2005 | Groemminger et al. ...... 510/112 |
| 6,919,321 | B2 | * | 7/2005 | Wang et al. .................... 514/54 |
| 7,218,802 | B1 | * | 5/2007 | Bellman et al. ................ 385/12 |

* cited by examiner

*Primary Examiner*—Maureen M Wallenhorst
(74) *Attorney, Agent, or Firm*—Sughrue Mion, PLLC (57) ABSTRACT

A sheath liquid for a particle analyzer used to analyze particles contained in a sample is described. The sheath liquid includes water and a refractive-index adjustment agent with glycerols and/or sulfate. A method for producing the sheath liquid and a method for analyzing particles using the sheath liquid are also described.

14 Claims, 6 Drawing Sheets

Slide a

Slide b

FIG. 3

Medium bottle a — Medium bottle b

FIG. 4

Medium bottle a — Medium bottle b

FIG. 5

Forward scattered light width

FIG. 6

Fluorescence intensity

SHEATH LIQUID FOR PARTICLE ANALYZER

BACKGROUND OF THE INVENTION

1. Field of the Invention

The present invention relates to a sheath liquid for a particle analyzer being used to analyze particles contained in a sample, a method for producing thereof, a method for analyzing particles using thereof.

2. Description of the Related Art

A particle analyzer based on flow cytometry is generally used to analyze particles in biological samples such as urine and blood. When a flow cytometer is used, the samples are enveloped in the stream of the sheath liquid and passed through a flow cell of the flow cytometer. Electrical or optical information from the samples when passing is detected by a detecting section in the flow cell, thereby analyzing particles contained in the samples.

An example of a known sheath liquid used for flow cytometer is described in U.S. Pat. No. 6,750,060. A large amount of sodium chloride is contained in this sheath liquid in order to adjust the refractive index of the sheath liquid. Use of the sheath liquid allows for accurate analysis of particles, even if a sample such as urine having a high refractive index is used as a specimen.

However, in the case where a device with the sheath liquid described in U.S. Pat. No. 6,750,060 is not used for a certain period, the precipitates may be accumulated in the interior of the device due to evaporation of the sheath liquid. Therefore, it is necessary to dismantle the device to remove the precipitates when accumulated. Additionally, materials which are highly anticorrosive to the sheath liquid may be used to make the metal portion of a device which comes in contact with the sheath liquid and regular part replacement may be needed, resulting in high production costs.

SUMMARY OF THE INVENTION

An objective of the present invention is to provide a sheath liquid by which precipitates are less likely produced and the metal portion of a device is less corroded. Further, the objective of the present invention is to provide a method of preparing the sheath liquid by which precipitates are less likely produced and the metal portion of a device is less corroded. Furthermore, the objective of the present invention is to provide a method for analyzing particles using the sheath liquid by which precipitates are less likely produced and the metal portion of a device is less corroded.

A first aspect of the present invention relates to a sheath liquid for use with a particle analyzer which analyzes particles in a sample, comprising water and a refractive-index adjustment agent comprising glycerols and/or sulfate.

A second aspect of the present invention relates to a method for producing a sheath liquid for a particle analyzer using a flow cytometer, comprising the steps of: providing water and a refractive-index adjustment agent comprising glycerols and/or sulfate; and mixing water and the refractive-index adjustment agent.

A third aspect of the present invention relates to a method for analyzing particles in a sample by a flow cytometer, comprising the steps of: enveloping the sample with a sheath liquid comprising water and a refractive-index adjustment agent comprising glycerols and/or sulfate; and passing the sample enveloped by the sheath liquid through a flow cell of the flow cytometer.

DESCRIPTION OF THE PREFERRED EMBODIMENTS

A sheath liquid in the embodiment is used for a particle analyzer based on flow cytometry. The particle analyzer based on flow cytometry has a flow cell. A sample is enveloped in the stream of the sheath liquid and passed through the flow cell of the device. Then electrical or optical information from the sample when passing is detected by a detecting section in the flow cell, thereby analyzing particles contained in the sample. The use of this device allows classification and counting of particles contained in samples, for example cells. The sheath liquid can be prepared by dissolving the substance for adjusting the refractive index (hereinafter referred to as refractive-index adjustment agent) in water.

The refractive index of sheath liquid used in the embodiment is not particularly limited as long as it does not affect the analysis of particles. Preferably, the refractive index of sheath liquid is an approximate value to the refractive index of the sample subjected to the measurement. Here, the term "an approximate value" means the value in the range of ±0.5% for the refractive index of a sample, preferably ±0.3%. When urine is used as a sample, it is preferable that the sheath liquid has a refractive index within the range of 1.338 to 1.345 at the wavelength of the sodium D line ($\lambda$=589.3 nm) at 25° C.

Refractive-index adjustment agents such as sulphate and/or glycerols are contained in the sheath liquid. The sheath liquid by which precipitates are less likely produced and the metal portion of a particle analyzer is less corroded can be provided by using sulphate and/or glycerols as refractive-index adjustment agents. The refractive-index adjustment agent is appropriately added so as to adjust the refractive index of sheath liquid to the desired range. The sheath liquid may contain sulphate and/or glycerols as main refractive-index adjustment agents. Further, it may contain refractive-index adjustment agents such as sodium chloride, potassium chloride, urea, sodium carbonate, sucrose, citrate, acetate, D-sorbitol, bicarbonate, and triethanolamine for auxiliary purposes such as fine adjustment of the refractive index. When sodium chloride is added to the sheath liquid, the concentration of sodium chloride is the concentration level in which a tube of the device is not clogged with precipitates of sodium chloride. Alternatively, when sodium chloride and/or potassium chloride are added to the sheath liquid, these concentrations are equal to the concentration levels in which the metal portion of the device is not corroded. When sodium chloride is used, the concentration is preferably 20 g/L or less, and more preferably 10 g/L or less.

As used herein, the term "glycerols" encompasses glycerol and a derivative of glycerol (hereinafter referred to as glycerol derivative). Examples of a glycerol derivative include thioglycerol, polyglycerol, and the like. Usable examples of polyglycerol may include diglycerol, POLYGLYCERIN #310 (Sakamoto Yakuhin Kogyo Co., Ltd.), POLYGLYCERIN #750 (Sakamoto Yakuhin Kogyo Co., Ltd.), POLYGLYCERIN #500 (Sakamoto Yakuhin Kogyo Co., Ltd.), and the like.

Examples of sulphate may include sodium sulfate, potassium sulfate, calcium sulfate, and the like.

In some cases, the electrical conductivity of sample may be measured when particles in the sample are analyzed with the particle analyzer. For example, it is known that the electrical conductivity of the urine correlates with the osmotic pressure or specific gravity of the urine. The urinary osmotic pressure or urinary specific gravity is used as an indicator of various diseases. For instance, low urinary specific gravity (1.010 or less) and low urinary osmotic pressure (200 mOsm/kg $H_2O$ or less) are observed most frequently in the impairment of urinary concentration such as diabetes insipidus and psychogenic polydipsia. On the other hand, high urinary specific gravity (1.030 or more) and high urinary osmotic pressure (850 mOsm/kg $H_2O$ or more) are observed most frequently in dehydration, prerenal failure, and the like.

High electrical conductivity of sheath liquid may affect the following measurements of samples (carry-over occurs), therefore the electrical conductivity of sheath liquid is preferable to be as low as possible. The electrical conductivity of sheath liquid is preferably 40 mS or less at 25° C., since the electrical conductivity of urine is from 5 to 30 mS at 25° C. in many cases. Thus, when the electrical conductivity of samples is measured, the carry-over can be controlled.

A pH of sheath liquid is preferably from 6.0 to 8.5, more preferably from 7.0 to 8.0. It is preferable to add a buffer agent to the sheath liquid in order to adjust the pH of sheath liquid. The kinds of buffer agents are not particularly limited as long as they adjust the pH of sheath liquid to the proper range. Examples of such a buffer agent include Good's buffers (specifically, tris buffers, MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, and the like), disodium hydrogenphosphate, sodium dihydrogen phosphate, monobasic potassium phosphate, veronal sodium-HCl, collidine-HCl, tris(hydroxymethyl)aminomethane-maleic acid, tris(hydroxymethyl)aminomethane-HCl, which may be used alone or in combination. It is preferable to use tris(hydroxymethyl)aminomethane-HCl or tris(hydroxymethyl)aminomethane-maleic acid among the buffer agents.

Introduction of the sheath liquid into the flow cell of the device may result in foam formation in the sheath liquid, which may cause a negative effect on measurements. Surface active agents may be added to the sheath liquid in order to control the foam formation. The kinds of surfactants are not particularly limited as long as they can control the foam formation. Any of cationic, anionic, nonionic, and ampholytic surfactants may be used. Specifically, polyoxyethylenealkyl ether-type surfactants, polyoxyethylenealkylphenyl ether-type surfactants (For example, NISSAN NONION NS-240 (NOF CORPORATION, registered trademark)), polyoxyethylenesorbitan alkyl ester-type surfactants (For example, RHEODOL TW-0120 (Kao Corporation, registered trademark)), polyol copolymers (For example, Pluronic P-105, P-84, P-85, P-87, P-75, and the like (BASF Corporation, registered trademark)), MEGA-8, sucrose monocaprate, deoxy-BIGCHAP, n-octyl-β-D-thioglucoside, n-nonyl-β-D-thiomaltoside, n-heptyl-β-D-thioglucoside, n-octyl-β-D-thioglucoside, CHAPS, CHAPSO, and the like may be used. The concentration of the surfactant in sheath liquid is preferably the concentration level in which the foam formation is controlled and particles such as cells in the sample are not affected. Specifically, the concentration is preferably from 5 to 5000 mg/L, more preferably from 100 to 3000 mg/L.

When particles contained in the sample are analyzed with the particle analyzer, amorphous salts such as ammonium phosphate, magnesium phosphate, calcium carbonate may precipitate in the sample. Chelating agents may be added to the sheath liquid in order to dissolve these amorphous salts. The addition of chelating agents enables not only dissolving amorphous salts, but also inhibiting the oxidation of sheath liquid. Usable examples of a chelating agent include EDTA salts, CyDTA, DHEG, DPTA-OH, EDDA, EDDP, GEDTA, HDTA, HIDA, Methyl-EDTA, NTA, NTP, NTPO, EDDPO, and the like. The concentration of the chelating agent in the sheath liquid is preferable within the range of 0.05 to 5 g/L.

Multiplication of microorganisms such as bacteria and fungi in the sheath liquid can affect analysis of particles in the sample. In order to inhibit multiplication of bacteria or fungi, substances which have fungicidal activity against the sheath liquid (fungicidal agents) and/or substances which have bactericidal activity against the sheath liquid (bactericidal agents) are added to the sheath liquid. Usable examples of fungicidal agents/bactericidal agents may include commercially-available products. Examples thereof include triazine antimicrobial agents, thiazole bactericidal agents (for example, benzisothiazolone etc.), pyrithione, pyridine bactericidal agents (for example, 1-hydroxy pyridine-2-thiosodium etc.), 2-phenoxyethanol, and the like. Specifically, Proxel GXL (Avecia), TOMICIDE S (API Corporation), and the like may be used.

The sample which is subjected to analysis using the particle analyzer with the sheath liquid in the embodiment is not particularly limited. The samples obtained from the living body (biological samples) can be used. Alternatively, those samples can be diluted, purified, dyed, or the like for use. Specifically, examples of such a sample may include urine, blood, semen, cerebrospinal fluid, and the like. The sheath liquid in the embodiment is suitably used when the particles in urine (red blood cell, white blood cell, bacteria, etc.) are analyzed.

Figure 1:
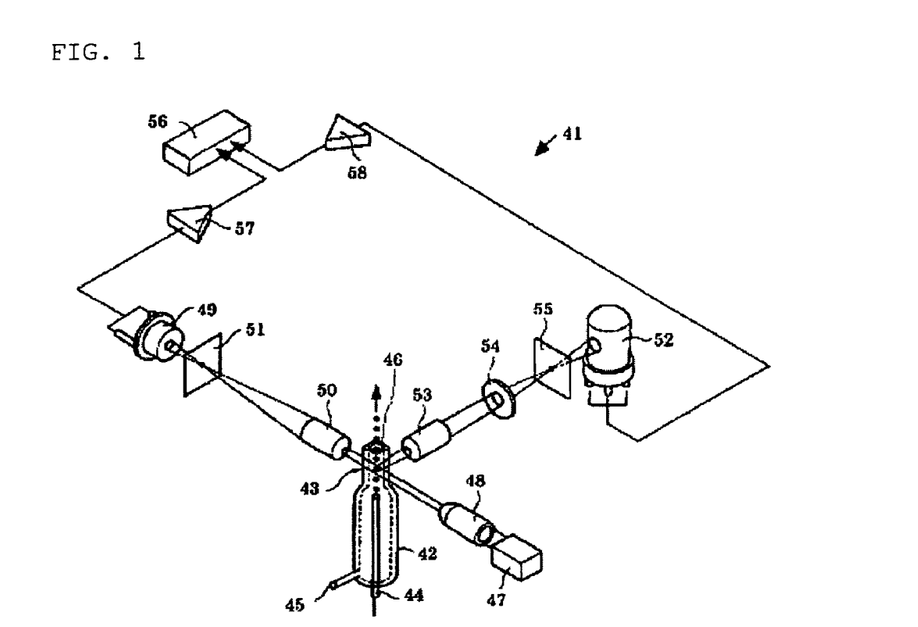
FIG. 1 is a schematic diagram of a flow cytometer of particle analyzer in which a sheath liquid in the embodiment is used.

In order to analyze the particles in the sample using the sheath liquid in the embodiment, a flow cytometer as shown in FIG. 1 can be used. A flow cell 42 for flowing a sample is a portion which is irradiated with a laser beam, the flow cell having: an orifice section 43 in which the internal flow passage is narrow; a nozzle 44 in which a sample is injected upward into the orifice section; a sheath liquid feed opening 45; and a waste liquid opening 46.

The flow cytometer 41 includes:

a condenser lens 48 which concentrates a laser beam emitted from a laser light source 47 to the flow cell 42;

a photodiode 49 which receives the forward scattered light emitted from the particles in the sample irradiated with the laser beam and then converts it into an electric signal;

a collector lens 50 and a pinhole 51 for concentrating the forward scattered light to the photodiode 49;

a photomultiplier tube 52 which receives the fluorescence emitted from the particles in the sample irradiated with the laser beam and then converts it into an electric signal;

a collector lens 53, a filter 54, and a pinhole 55 for concentrating fluorescence to the photomultiplier tube 52; and an amplifier 57 which amplifies the electric signal output from the photodiode 49, and outputs it to an analyzing section 56 as a forward scattered light signal;

an amplifier 58 which amplifies the electric signal output from the photomultiplier tube 52, and outputs it to an analyzing section 56 as a fluorescence signal.

When the sample is passed through the flow cell 42, each time when the particles contained in the sample pass through the irradiation area of the laser beam emitted from the laser light source 47, fluorescence and scattered light are produced. Side fluorescence is received and photoelectrically converted by the photomultiplier tube 52, and forward scattered light is received and photoelectrically converted by the photodiode 49, which are output to the analyzing section 56 as light detecting signals such as a side fluorescence signal and a forward scattered light signal.

The analyzing section 56 is composed of a computer consisting of a circuit which amplifies a light detecting signal for each particle detected by the flow cytometer 41 and removes a noise, CPU, ROM, RAM, and the like. The analyzing section 56 analyzes the light detecting signal for each particle detected by the flow cytometer 41 and creates a scattering diagram to count the particles contained in the sample. The analyzing section 56 calculates forward scattered light intensity and forward scattered light width based on a forward scattered light signal and also calculates fluorescence intensity based on a side fluorescence signal. A scattering diagram is constructed using combinations of these parameters and then the kind and number of each particle in the sample are analyzed.

EXAMPLE 1

The following substances were dissolved in 1 kg of purified water to prepare a sheath liquid.
Tris(hydroxymethyl)aminomethane 1.51 g
Hydrochloric acid 6 mol
EDTA-2K 0.2 g
RHEODOL TW0120V 0.75 g
TOMICIDE S 0.2 g
Proxel GXL 0.2 g Different kinds of refractive-index adjustment agents were added to the above-mentioned sheath liquid. Then we examined how much refractive-index adjustment agents should be added in order to adjust the refractive index of sheath liquid to 1.342. Digital refractometer RX-5000 α (ATAGO CO., LTD.) was used for measurements of refractive index. The refractive index was measured at 25° C.

As a result of our examination, it was found that, in the case where glycerol was used as a refractive-index adjustment agent, addition of glycerol at a concentration of 79 g/L to the sheath liquid allowed the adjustment of the refractive index to 1.342.

It was found that, in the case where thioglycerol was used as a refractive-index adjustment agent, addition of thioglycerol at a concentration of 57 g/L to the sheath liquid allowed the adjustment of the refractive index to 1.342.

It was found that, in the case where diglycerol was used as a refractive-index adjustment agent, addition of diglycerol at a concentration of 69 g/L to the sheath liquid allowed the adjustment of the refractive index to 1.342.

It was found that, in the case where POLYGLYCERIN #310 was used as a refractive-index adjustment agent, addition of POLYGLYCERIN #310 at a concentration of 71 g/L to the sheath liquid allowed the adjustment of the refractive index to 1.342.

It was found that, in the case where POLYGLYCERIN #750 was used as a refractive-index adjustment agent, addition of POLYGLYCERIN #750 at a concentration of 73 g/L to the sheath liquid allowed the adjustment of the refractive index to 1.342.

It was found that, in the case where POLYGLYCERIN #500 was used as a refractive-index adjustment agent, addition of POLYGLYCERIN #500 at a concentration of 75 g/L to the sheath liquid allowed the adjustment of the refractive index to 1.342.

It was found that, in the case where sodium sulfate was used as a refractive-index adjustment agent, addition of sodium sulfate at a concentration of 62 g/L to the sheath liquid allowed the adjustment of the refractive index to 1.342.

It was found that, in the case where sodium chloride and glycerol were used as refractive-index adjustment agents, addition of sodium chloride and glycerol at concentrations of 7.1 g/L and 69.1 g/L, respectively, to the sheath liquid allowed the adjustment of the refractive index to 1.342.

It was found that, in the case where sodium chloride and sodium sulfate were used as refractive-index adjustment agents, addition of sodium chloride and sodium sulfate at concentrations of 7.1 g/L and 54.44 g/L, respectively, to the sheath liquid allowed the adjustment of the refractive index to 1.342.

It was found that, in the case where sodium chloride, sodium sulfate, and glycerol were used as refractive-index adjustment agents, addition of sodium chloride, sodium sulfate, and glycerol at concentrations of 7.1 g/L, 28.45 g/L, and 34 g/L, respectively, to the sheath liquid allowed the adjustment of the refractive index to 1.342.

EXAMPLE 2

Different kinds of refractive-index adjustment agents were added to the sheath liquid in Example 1 in order to adjust the refractive index of sheath liquid to 1.342, and then the electrical conductivity was measured. Electrical Conductivity Meter DS-8F (HORIBA, Ltd.) was used for measurements of electrical conductivity.

7.1 g/L of sodium chloride and 69.1 g/L glycerol were added as refractive-index adjustment agents to the sheath liquid, and a sheath liquid A was prepared. The electrical conductivity of the sheath liquid A was 11 mS.

7.1 g/L of sodium chloride, 28.45 g/L of sodium sulfate, and 34 g/L glycerol were added as refractive-index adjustment agents to the above-mentioned sheath liquid to prepare a sheath liquid B. The electrical conductivity of the sheath liquid B was 35 mS.

79 g/L of glycerol was added as a refractive-index adjustment agent to the sheath liquid to prepare a sheath liquid C. The electrical conductivity of the sheath liquid C was 1.1 mS.

As mentioned above, it is considered that the carry-over is less produced during the measurement since each of sheath liquids A to C has a refractive index of 1.342 and an electrical conductivity of 40 mS or less.

EXAMPLE 3

We examined whether precipitation of salts would be observed using the sheath liquid A prepared in Example 2. As a control, to the sheath liquid in Example 1, sodium chloride was added at a concentration of 55 g/L as a refractive-index adjustment agent in order to prepare a sheath liquid D.

100 µL of the sheath liquid A and 100 µL of the sheath liquid D were dropped on slide glasses, respectively, which were dried at 25° C.

Figure 2:
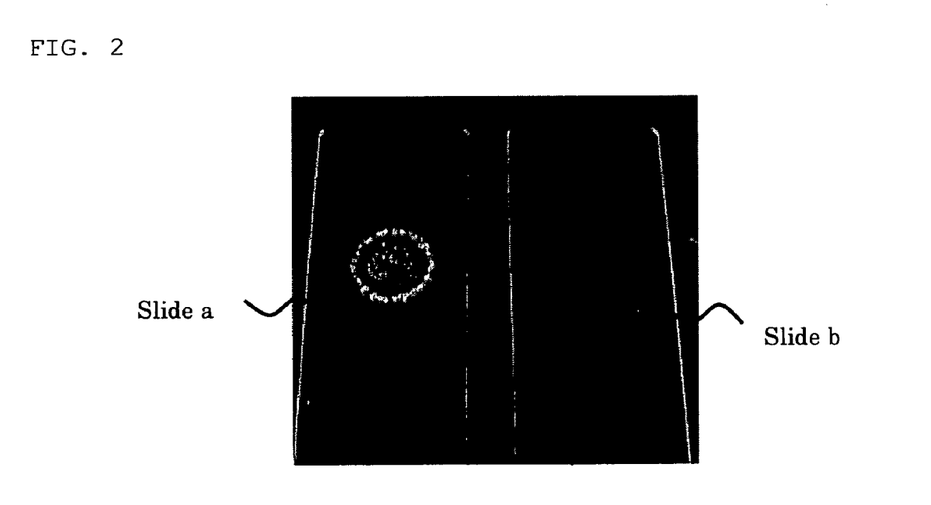
FIG. 2 shows a photograph of a slide glass (slide a) after dropping a sheath liquid D and drying it, and a slide glass (slide b) after dropping a sheath liquid A and drying it.

A photograph of the slide glasses after dryness is shown in FIG. 2. A slide a indicates the slide glass on which the sheath liquid D was dropped, and a slide b indicates the slide glass on which the sheath liquid A was dropped. As shown in FIG. 2, when the sheath liquid D was dried, precipitation of salts was observed. However, when the sheath liquid A was dried, little precipitation was observed. As mentioned above, it is considered that the tube is less clogged with precipitation of salts in the case where the sheath liquid A is used for the particle analyzer.

EXAMPLE 4

We examined whether precipitation of salts would be observed using the sheath liquid B prepared in Example 2. As a control, the sheath liquid D prepared in Example 3 was used. 100 mL of the sheath liquid A and 100 mL of sheath liquid D were charged into the medium bottles, respectively, which were dried at 60° C. until all water had evaporated.

Figure 3:
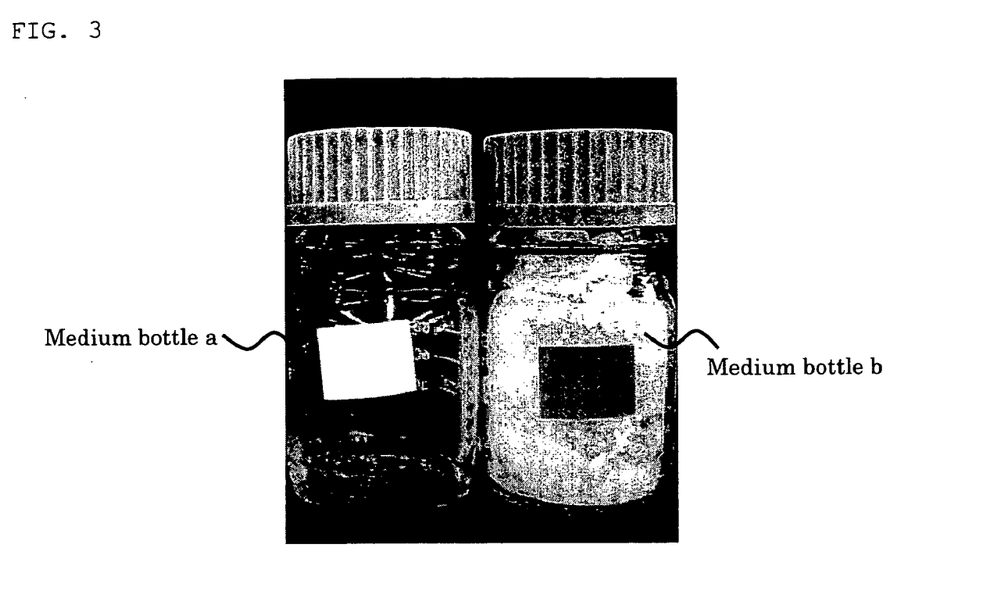
FIG. 3 shows a photograph from the side of a medium bottle (medium bottle a) after evaporating a sheath liquid B, and a photograph from the side of a medium bottle (medium bottle b) after evaporating a sheath liquid D.
Figure 4:
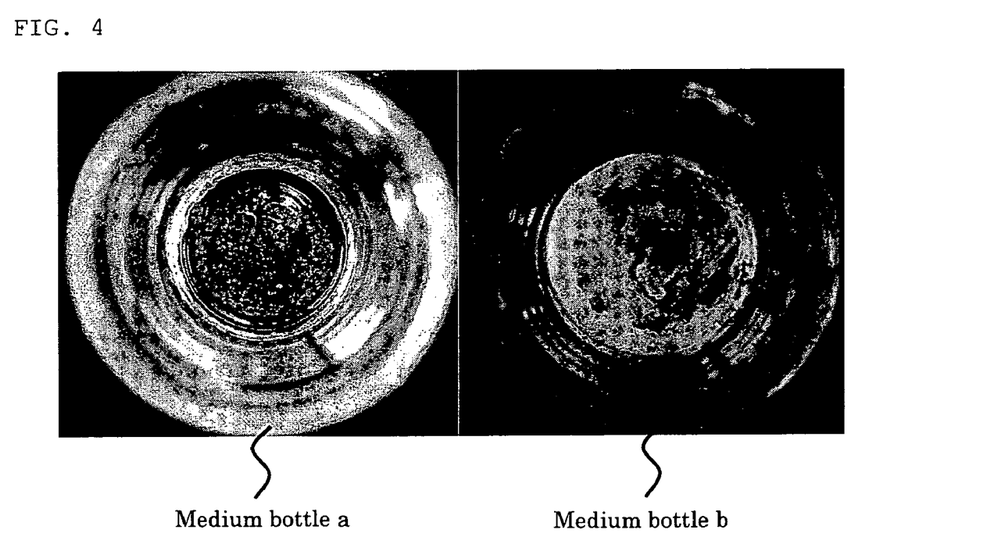
FIG. 4 shows a photograph from the side of medium bottle a in FIG. 3, and a photograph from the side of medium bottle b in FIG. 3.

A photograph of the medium bottles after dryness is shown in FIGS. 3 and 4. FIG. 3 shows a photograph from the side of the medium bottle (medium bottle a) after evaporation of the sheath liquid B and a photograph from the side of the medium bottle (medium bottle b) after evaporation of the sheath liquid D. FIG. 4(*a*) shows a photograph of the interior of medium bottle a in FIG. 3, and FIG. 4(*b*) shows a photograph of the interior of medium bottle b in FIG. 3. As is apparent from FIGS. 3 and 4, when the sheath liquid B was dried, only a little precipitation of salts was observed. However, when the sheath liquid D was dried, large amounts of precipitation of salts were observed. As mentioned above, it is considered that the tube is less clogged with precipitation of salts in the case where the sheath liquid B is used for the particle analyzer.

EXAMPLE 5

The sheath liquid B prepared in Example 2 was applied for Bacteria Analyzer BACSYS-40i (manufactured by Sysmex Corporation) and BACTCHECK (manufactured by Sysmex Corporation) which is a quality control substance was used as a sample. Mimic particles (hereinafter referred to as mimic bacteria) correspond to the bacteria in the sample and mimic particles (hereinafter referred to as mimic white blood cells) correspond to the white blood cells in the sample were measured.

50 µL of BACTCHECK, 10 µL of stain solution, Measuring Reagent "BACTCATCH" (manufactured by Sysmex Corporation) used for the Bacteria analyzer, and 340 µL of diluent were mixed. The mixed solutions were introduced into the flow cell of particle analyzer, and the side fluorescence signal and forward scattered light signal generated by particles contained in the sample were given. The fluorescence intensity was calculated from the side fluorescence signal, and the forward scattered light intensity 1, the forward scattered light intensity 2, and the forward scattered light width were calculated from the forward scattered light signal. The degree of signal amplification differs between the forward scattered light intensity 1 and the forward scattered light intensity 2. Consequently, the forward scattered light intensity 1 is used for the measurement of mimic bacteria, and the forward scattered light intensity 2 is used for the measurement of mimic white blood cells.

Figure 5:
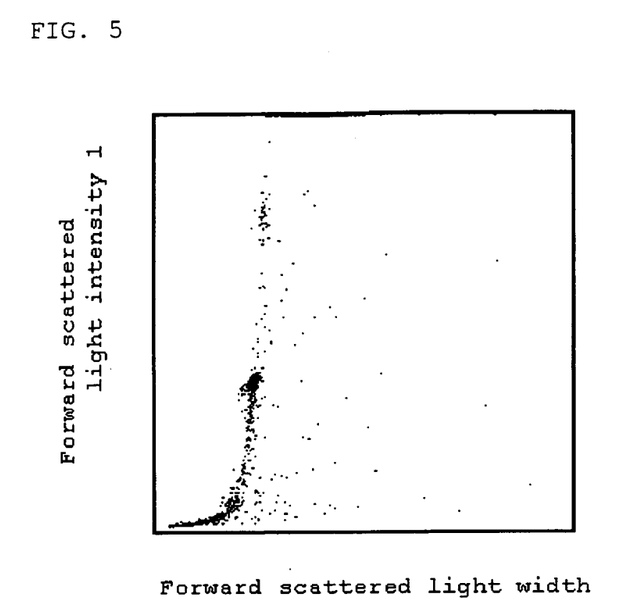
FIG. 5 is a scattering diagram used when counting mimic bacteria using the sheath liquid B.
Figure 6:
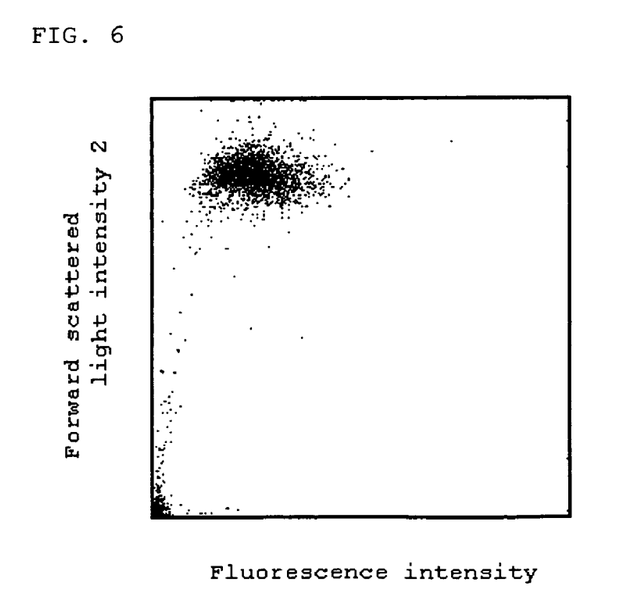
FIG. 6 is a scattering diagram used when counting mimic white blood cells using the sheath liquid B.

A scattering diagram in which the forward scattered light width and the forward scattered light intensity 1 were used as two axes was constructed, and the mimic bacteria were counted. The scattering diagram is shown in FIG. 5. A scattering diagram in which the fluorescence intensity and the forward scattered light intensity 2 were used as two axes was constructed, and the mimic white blood cells were counted. The scattering diagram is shown in FIG. 6. The measurement was performed 8 times, The measurement results are shown in the Table 1 below. In table 1, "BACT" shows the mimic bacterial counts (/µL). "WBC" shows the mimic white blood cell counts (/µL). "FSLI 1" shows the forward scattered light intensity 1. "FSLIW" shows the forward t scattered light width. "FSLI 2" shows the forward scattered light intensity 2. "FI" shows the fluorescence intensity.

TABLE 1

| | Measurement | BACT | WBC | FSLI 1 | FSLW | FSLI 2 | FI |
|---|---|---|---|---|---|---|---|
| Sheath liquid B | 1 | 454.1 | 500.6 | 91.5 | 60 | 211 | 62.5 |
| | 2 | 466.6 | 500 | 92 | 60 | 210 | 59 |
| | 3 | 458.9 | 482.9 | 91 | 60 | 208.5 | 59 |
| | 4 | 486.6 | 507.2 | 91 | 60 | 209.5 | 58.5 |
| | 5 | 477.3 | 502.7 | 92 | 61 | 210 | 57.5 |
| | 6 | 473.1 | 493.6 | 92 | 60.5 | 209.5 | 56.5 |
| | 7 | 466.3 | 470.2 | 92.5 | 60 | 211 | 62 |
| | 8 | 483.4 | 492.7 | 91.5 | 60 | 210 | 61 |
| Average | | 470.8 | 493.7 | 91.7 | 60.2 | 209.9 | 59.5 |
| CV(%) | | 2.40% | 2.40% | 0.60% | 0.60% | 0.40% | 3.60% |

Figure 7:
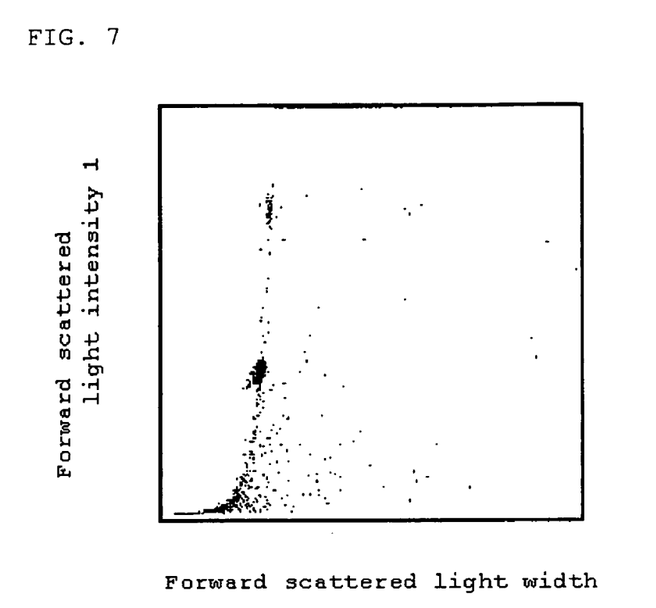
FIG. 7 is a scattering diagram used when counting mimic bacteria using BACTSHEATH.
Figure 8:
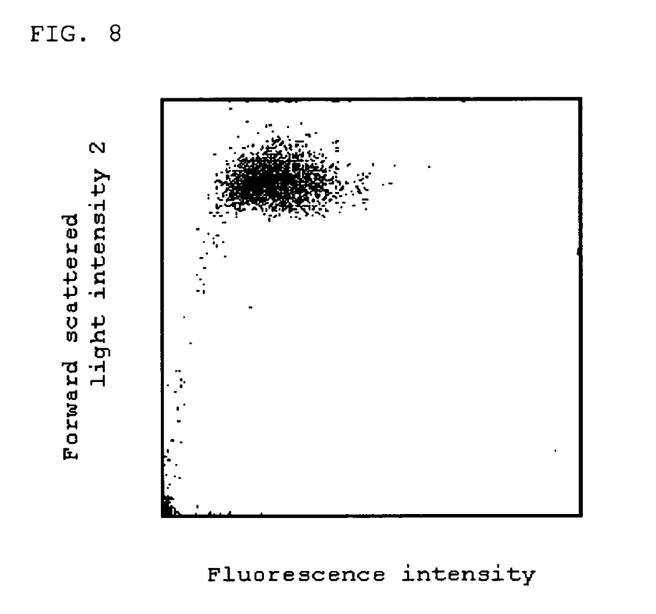
FIG. 8 is a scattering diagram used when counting mimic white blood cells using BACTSHEATH.

Further, the mimic bacteria and the mimic white blood cells were counted in the same manner as described above using BACTSHEATH (manufactured by Sysmex Corporation) which is a sheath liquid used for the above-mentioned device as a control. A scattering diagram in which the forward scattered light width and the forward scattered light intensity 1 were used as two axes were shown in FIG. 7. A scattering diagram in which the fluorescence intensity and the forward scattered light intensity 2 were used as two axes was shown in FIG. 8. The measurement was performed 8 times. The measurement results are shown in the Table 2 below.

TABLE 2

|  | Measurement | BACT | WBC | FSLI 1 | FSLW | FSLI 2 | FI |
|---|---|---|---|---|---|---|---|
| Bactsheath (Control) | 1 | 480.4 | 484.6 | 90.5 | 61 | 205.5 | 62.5 |
|  | 2 | 502.6 | 486.6 | 90 | 61 | 206 | 62.5 |
|  | 3 | 483.8 | 490.4 | 90 | 61 | 205 | 62 |
|  | 4 | 485.7 | 471 | 90 | 61 | 206 | 63 |
|  | 5 | 508.7 | 475.2 | 90 | 61 | 206 | 57.5 |
|  | 6 | 499.4 | 500.3 | 90 | 61 | 205.5 | 63 |
|  | 7 | 510 | 474.9 | 91.5 | 61 | 208 | 65 |
|  | 8 | 482 | 491.3 | 90.5 | 61 | 208 | 70 |
| Average |  | 494.1 | 484.3 | 90.3 | 61 | 206.3 | 63.2 |
| CV(%) |  | 2.50% | 2.10% | 0.60% | 0.00% | 0.50% | 5.50% |

As is apparent from Tables 1 and 2, either the sheath liquid B or BACTSHEATH were used, the mimic bacterial counts, mimic white blood cell counts, signal strength, and CV (coefficient of variation) of signal width were extremely low in eight measurements. The mimic bacterial counts and mimic white blood cell counts which were quantified using BACT-SHEATH were approximated to the mimic bacterial counts and mimic white blood cell counts which were quantified using the sheath liquid B. As mentioned above, it was confirmed that particles in the sample could be measured accurately and reproducibly as with conventional sheath liquids when the sheath liquid B was used.

EXAMPLE 6

Figure 9:
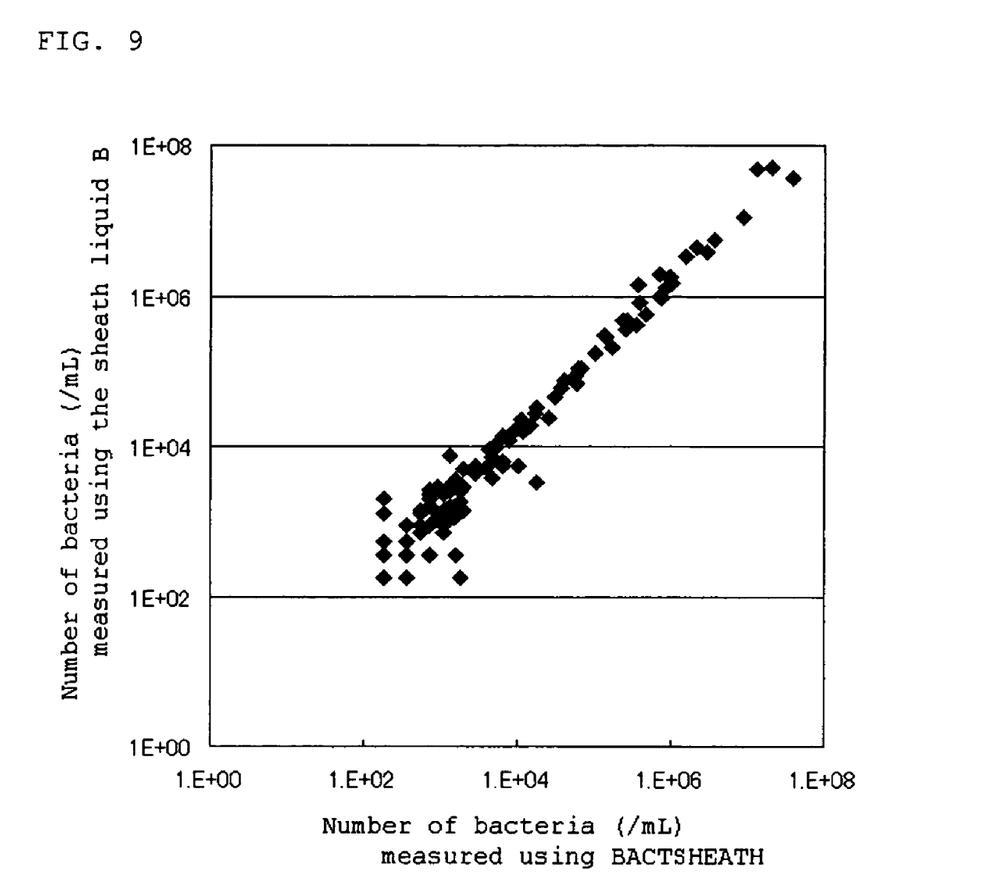
FIG. 9 shows a graph of correlation between the bacterial count measured using the sheath liquid B and the bacterial count measured using BACTSHEATH.
Figure 10:
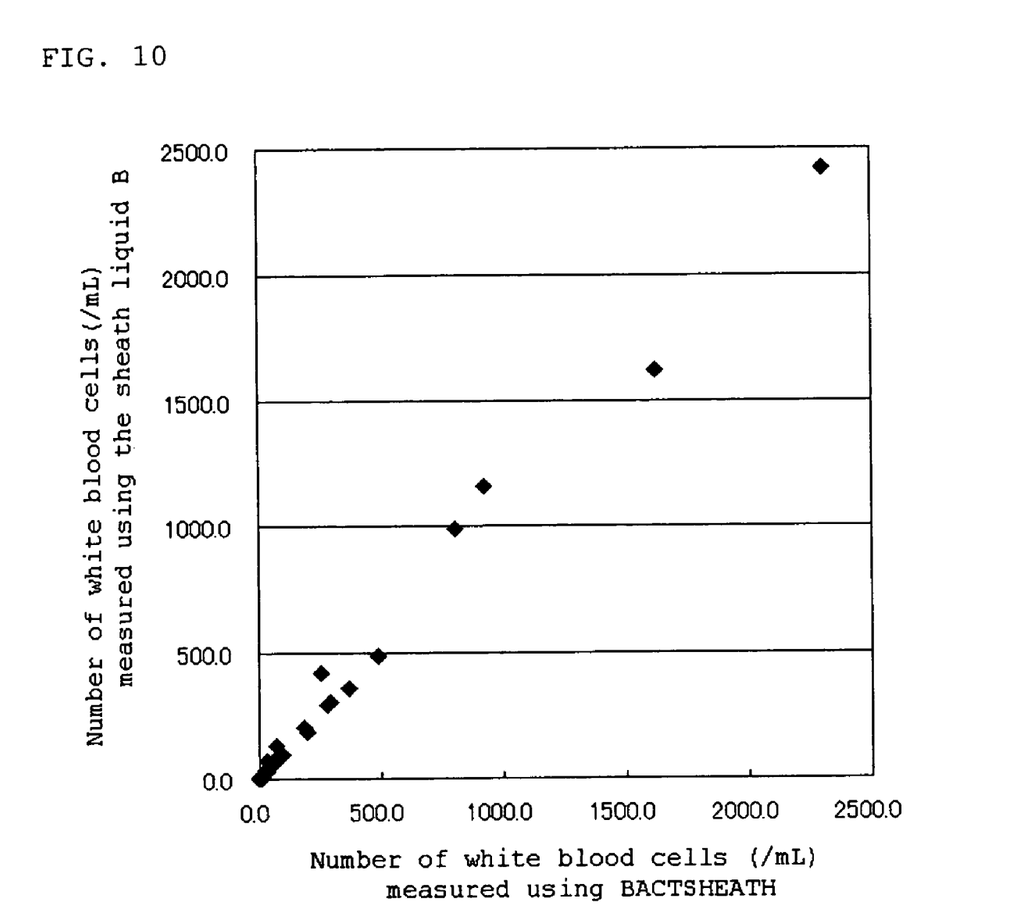
FIG. 10 shows a graph of correlation between the white blood cell count measured using the sheath liquid B and the white blood cell count measured using BACTSHEATH.

The bacterial counts and white blood cell counts in 116 specimens, i.e., 116 urine samples (specimen numbers 1 to 116) were quantified in the same manner as Example 5 using the sheath liquid B. Alternatively, the bacterial counts and white blood cell counts of the 116 samples were quantified using BACTSHEATH as a control. A correlation graph between the bacterial counts quantified using the sheath liquid B and the bacterial counts quantified using BACT-SHEATH is shown in FIG. 9. A correlation graph between the white blood cell counts quantified using the sheath liquid B and the white blood cell counts quantified using BACT-SHEATH is shown in FIG. 10.

As shown in FIG. 9, it was found that the bacterial counts quantified using the sheath liquid B were significantly correlated with the bacterial counts quantified using BACT-SHEATH. In addition, as shown in FIG. 10, it was found that the white blood cell counts quantified using the sheath liquid B were significantly correlated with the white blood cell counts quantified using BACTSHEATH. As mentioned above, it was confirmed that the particles in the specimen could be accurately measured as with conventional sheath liquids when the sheath liquid B was used.

What is claimed is:

1. A sheath liquid for use with a flow cytometer which analyzes particles in a urine sample, comprising:
   water:
   at least one selected from glycerol and glycerol derivative;
   10 g/L or less of sodium chloride;
   a buffer agent; and
   a chelating agent,
   wherein when the urine sample is enveloped by the sheath liquid, the sheath liquid has a refractive index within the range of 1.338 to 1.345 at a wavelength of sodium D line at 25° C. and a concentration of sodium chloride of 10 g/L or less, and the urine sample enveloped by the sheath liquid passes through a flow cell of the flow cytometer.

2. The sheath liquid according to claim 1, wherein the glycerol derivative is selected from the group consisting of thioglycerol and polyglycerol.

3. The sheath liquid according to claim 1, having an electrical conductivity of 40 mS or less at 25° C.

4. The sheath liquid according to claim 1, wherein the buffer agent comprises tris(hydroxymethyl)aminomethane-HCl and/or tris(hydroxymethyl)aminomethane-maleic acid.

5. The sheath liquid according to claim 1, further comprising at least one substance selected from the group consisting of a surfactant, sulfate and a fungicidal agent/bactericidal agent.

6. A method for producing a sheath liquid for a particle analyzer of a urine sample using a flow cytometer, comprising the steps of:
   providing water, a buffer agent, a chelating agent, sodium chloride and at least one selected from glycerol and glycerol derivative to obtain a mixture; and
   mixing the water, the buffer agent, the chelating agent, the sodium chloride and the at least one selected from glycerol and glycerol derivative to obtain a mixture;
   wherein when the urine sample is enveloped by the obtained mixture, the obtained mixture has a sodium chloride concentration of 10 g/L or less, and has a refractive index within the range of 1.338 to 1.345 at a wavelength of sodium D line at 25° C., and the urine sample enveloped by the obtained mixture passes through a flow cell of the flow cytometer.

7. The method according to claim 6, wherein the glycerol derivative is selected from the group consisting of thioglycerol and polyglycerol.

8. The method according to claim 6, wherein the mixture obtained by the mixing step has an electrical conductivity of 40 mS or less at 25° C.

9. The method according to claim 6, wherein the buffer agent comprises tris(hydroxymethyl)aminomethane-HCl and/or tris(hydroxymethyl)aminomethane-maleic acid.

10. The method according to claim 6 comprising,
    further providing at least one substance selected from the group consisting of a surfactant, sulfate, and a fungicidal agent/bactericidal agent in the providing step, and
    further mixing the at least one substance in the mixing step.

11. A method for analyzing particles in urine by a flow cytometer, comprising the steps of:
    enveloping a urine sample with a sheath liquid comprising water, a buffer agent, a chelating agent, 10 g/L or less of sodium chloride, and at least one selected from glycerol and glycerol derivative; and
    passing the urine sample enveloped by the sheath liquid through a flow cell of the flow cytometer, wherein the sheath liquid has a refractive index within the range of 1.338 to 1.345 at a wavelength of sodium D line at 25° C.

12. The method according to claim 11, further comprising the steps of:
   detecting optical information from particles in the urine sample passing through the flow cell; and
   analyzing particles based on the optical information.

13. The method according to claim 12, wherein the optical information comprises scattered light and/or fluorescence.

14. The method according to claim 11,
   wherein the sheath liquid further comprises at least one substance selected from the group consisting of a surfactant, sulfate, and a fungicidal agent/bactericidal agent.

* * * * *